United States Patent [19]

Sultenfuss

[11] Patent Number: 5,281,196
[45] Date of Patent: Jan. 25, 1994

[54] SKIN TREATMENT COMPOSITION AND METHOD OF USE

[76] Inventor: Thomas J. Sultenfuss, 102 Harbor View La., Largo, Fla. 34640

[21] Appl. No.: 887,481

[22] Filed: May 22, 1992

[51] Int. Cl.$^5$ .............................................. A61N 1/30
[52] U.S. Cl. ..................................... 604/20; 604/49; 128/898
[58] Field of Search ................... 604/20, 49; 128/898

[56] References Cited

U.S. PATENT DOCUMENTS

| | | | |
|---|---|---|---|
| 4,578,390 | 3/1986 | Jensen et al. | 514/472 |
| 4,617,187 | 10/1986 | Okuyama et al. | 514/689 |
| 4,670,471 | 6/1987 | Clark | 514/859 |
| 4,686,235 | 8/1987 | Chang et al. | 514/522 |
| 4,707,354 | 11/1987 | Garlen et al. | 514/847 |
| 4,861,783 | 8/1989 | Ackerman et al. | 514/861 |
| 4,975,272 | 12/1990 | Voyt | 514/847 |
| 5,078,129 | 1/1992 | Kleinberg et al. | 128/200.21 |

Primary Examiner—C. Fred Rosenbaum
Assistant Examiner—Michael Rafa
Attorney, Agent, or Firm—Dominik, Stein, Saccocio, Reese, Colitz & Van Der Wall

[57] ABSTRACT

A composition and method of applying a composition of (a) between about 10 and 15 percent vitamin C, plus or minus 10 percent, by weight to volume, (b) a viscosity agent, and (c) water as the remainder of the composition to healthy surface tissue overlying unhealthy tissue to be treated by radiation therapy for thereby abating dermatitis, mucositis, and esophagitis normally attendant with radiation therapy, the method comprising the steps of identifying the healthy surface tissue in the path of a radiation beam proposed to treat the unhealthy tissue, the identified healthy tissue being pretreated with vitamin C to increase the concentration of ascorbic acid in the identified healthy tissue; applying the composition to the identified healthy tissue; waiting a period of time of about at least one hour prior to radiation therapy so as to allow the vitamin C of the composition to increase the concentration of ascorbic acid in the healthy tissue whereby free radicals from ensuing radiation therapy are scavenged by the increased concentration of ascorbic acid in the healthy tissue; applying therapeutic radiation to the pretreated healthy tissue and the unhealthy tissue in a predetermined target dosage so that unhealthy tissue will be destroyed but so that the increased concentration of ascorbic acid in the healthy tissue will scavenge free radicals from the applied radiation; and scavenging free radicals from the applied radiation by the increased concentration of ascorbic acid in the healthy tissue so that dermatitis, mucositis, and esophagitis normally resulting from radiation therapy are abated.

11 Claims, 2 Drawing Sheets

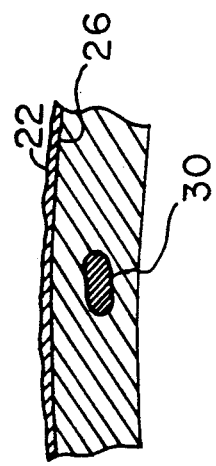
F I G. IA
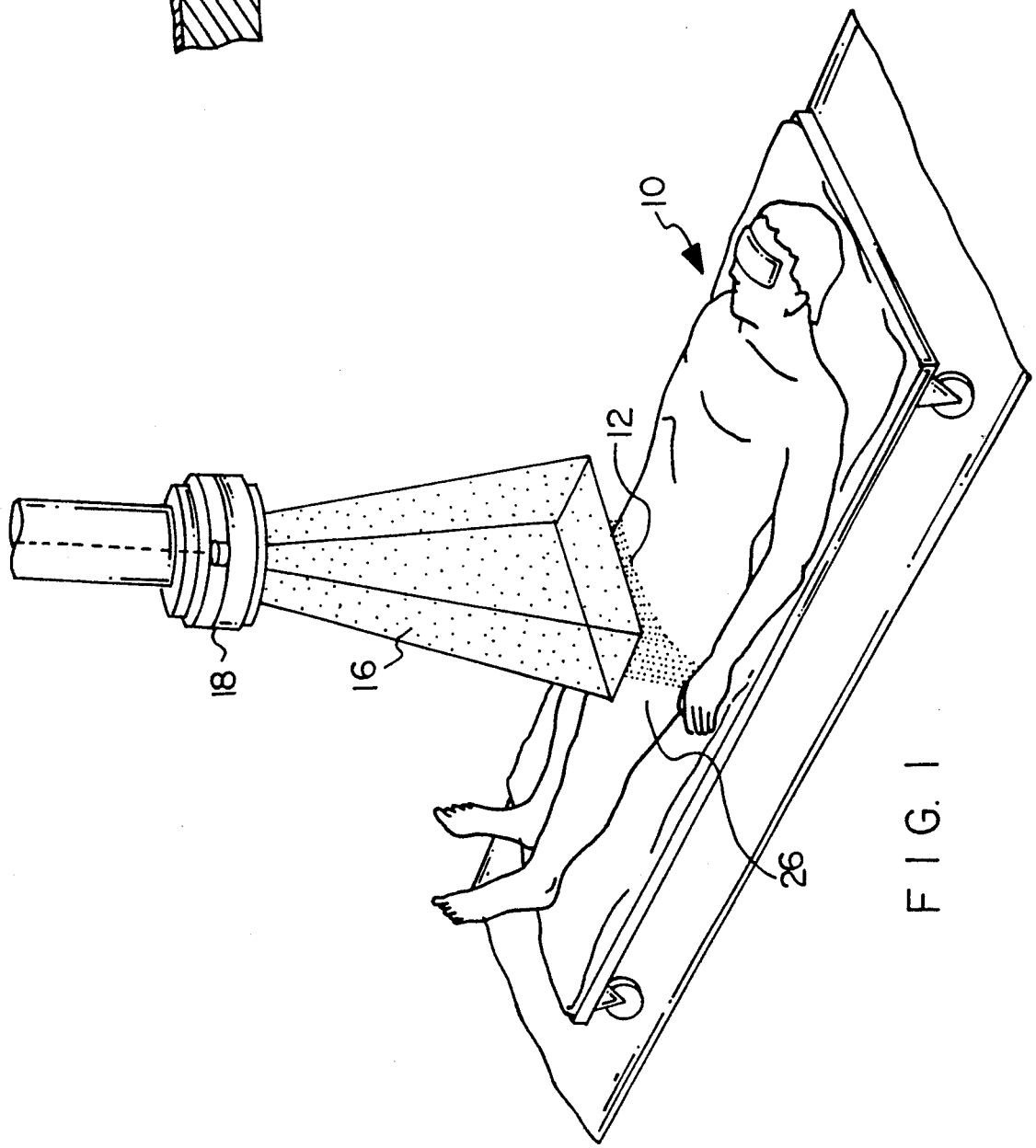
F I G. I

SKIN TREATMENT COMPOSITION AND METHOD OF USE

BACKGROUND OF THE INVENTION

Summary of the Invention

This invention relates to a skin treatment composition and method of use, and more particularly, to a skin treatment composition and method of therapeutic use comprising Vitamin C or its salts for the prevention of dermatitis, mucositis and esophagitis as side effects of radiation therapy.

Description of the Background Art

In the field of radiation therapy, there have been a variety of compounds created to facilitate the protection of healthy tissue surrounding cancerous cells during high-energy radiation treatment of the cancerous cells. Acute dermatitis, mucositis and esophagitis are well recognized as constituting normal common side effects of high-energy radiation treatment in humans. Dermatitis, mucositis and esophagitis are not only uncomfortable, but also potentially debilitating. Furthermore, these side effects cause undesirable delays in the application of rehabilitative therapy to the patient. Therefore, for protecting healthy tissue from the damaging side effects that result from the radiation treatment, many patients receive a topical agent for application to the area of skin to be exposed to radiation. Many types of compounds, such as topical cortisones, almond oil and chamomile cream have been tried unsatisfactorily for alleviating dermatitis that normally result from radiation treatment. Never have such materials been used for mucositis or and esophagitis. However, vitamin C has been shown to ameliorate radiation mucositis after systemic administration.

The present invention is directed to improving skin treatment compositions and methods of use for the prevention of dermatitis, mucositis and esophagitis as side effects of radiation therapy in a manner which is safe, convenient and economical.

It is well known within the medical profession that vitamin C is a major anti-oxidant agent found within the human body. The anti-oxidant property of the vitamin C protects tissues from damage caused by the abundant oxygen found within the earth's atmosphere. The human body, however, cannot manufacture vitamin C. Therefore, vitamin C must be supplied to the body, generally through dietary sources. Normally, the human body can only absorb 1200 mg to 3000 mg of vitamin C per day through the gastrointestinal tract. Additionally, the body's kidneys will excrete vitamin C if blood plasma levels exceed about 1.4 mg percent. The body has the ability to store approximately 1500 mg of vitamin C. The amount of Vitamin C levels in bodily tissues varies. The skin, however, is about average with a 0.2 to 0.3 millimolar concentration of vitamin C.

Throughout the United States steps are being taken to improve upon compositions for improving skin treatment compositions and methods of use for the prevention of dermatitis, mucositis and esophagitis as side effects of radiation therapy.

The prior art discloses several methods of incorporating vitamin C into cosmetic products for a variety of purposes, including the treatment of aging and photo-damaged skin, bleaching skin and regeneration of collagen. By way of example, U.S. Pat. Nos. 4,668,516 to Duraffourd et al; 4,938,969 to Schinitsky; and 4,518,614 to Parkinson disclose cosmetic compositions containing vitamin C. A composition for the regeneration of the collagen of connective skin tissue was disclosed in the U.S. Pat. No. 4,668,516. The composition is for treating wrinkles by regenerating the collagen of the connective tissue of the skin by application of the solution to the skin. A composition for reducing wrinkle depth or intensity is disclosed in the U.S. Pat. No. 4,938,969. The composition in an ointment or cream base contains ascorbic salt for topical application to the skin for the reduction of wrinkles therein. The U.S. Pat. No. 4,518,614 relates to a composition containing ascorbic acid for moisturizing and softening skin for improving the texture thereof and diminishing superficial and deep wrinkles therein. None of these disclosures teaches or suggests a composition for improving skin treatment compositions or methods of use for the prevention of dermatitis, mucositis and esophagitis as side effects of radiation therapy.

The prior art discloses compositions for skin whitening cosmetics in U.S. Pat. Nos. 5,078,989 to Ando et al and 4,919,921 to Hatae. Neither of the disclosures, however, teaches nor suggests a composition for the prevention of dermatitis, mucositis and esophagitis as side effects of radiation therapy.

Further U.S. Pat. Nos. 4,983,382 to Wilmott et al and 4,818,521 to Tamabuchi disclose compositions containing stabilized ascorbic acid. The U.S. Pat. No. 4,983,382 relates to a cosmetic preparation incorporating a stabilized ascorbic acid. The composition is topically applied to the skin to impart a beneficial appearance thereto. Additionally, the U.S. Pat. No. 4,818,521 relates to a emulsion cosmetic stably containing vitamin C. The emulsion contains vitamin C stably formulated for formulating into a cosmetic use. Neither disclosure relates to the prevention of radiation side effects of dermatitis, mucositis and esophagitis.

Moreover, it has been shown that a topical application of vitamin C to human skin is absorbed percutaneously. S. R. Pinnell, "Tropical Vitamin C: A New Approach for Photoaging", Lecture delivered at the 1991 American Academy of Dermatology 50th Annual Meeting, Dec. 11, 1991. Additionally, vitamin C is protective against sunburn from ultraviolet A-range and ultraviolet B-range light. The vitamin C does not act as a sunblock, rather it acts to prevent the chain of events that leads from energy deposition to tissue damage and inflammation. The article, however, discloses a method of preventing sunburn, the article does not teach or suggest a composition or method of preventing dermatitis, mucositis and esophagitis resulting from radiation treatment.

Additionally, U.S. patent application Ser. No. 399,386 to Zimmerman et al, filed Aug. 25, 1989, proposed a method of using a free radical scavenger as an adjunct to tumor necrosis factor or other cytokines and lymphokines for treating tissue damage caused by a variety of insults. The free radical scavengers proposed were vitamin C, uric acid and aspirin among others. The application does not disclose a composition for use to prevent dermatitis, mucositis and esophagitis that normally result from radiation therapy.

Finally, it has been show that prophylactic systemic administration of vitamin C significantly reduces the inflammation of the mucosa of the oral cavity in patients receiving radiation therapy for head and neck cancer. R. Garcia et al, "Effecto Radioprotector del Acido Ascorbico sobre Estructuras Orales en Patientes con Cancer de Cabeza y Cuello", *Avances en Odontoestomatologia* 1989, Volume 5; pages 469–472. In the Garcia disclosure, however, the amount of vitamin C a patient's body has available to prevent damage is limited by the body's ability to absorb, and for the kidneys to retain, vitamin C through the gastrointestinal tract or through injection.

As illustrated by the background art, efforts are continuously being made in an attempt to improve skin treatment compositions and their methods of use for the prevention of dermatitis, mucositis and esophagitis as side effects of radiation therapy. No prior effort, however, provides the benefits attendant with the present invention. Additionally, the prior patents, patent applications and commercial techniques do not suggest the present inventive composition of elements combined as disclosed and claimed herein.

The present invention achieves its intended purposes, objects, and advantages through a new, useful and unobvious combination of method steps and component elements, with the use of a minimum number of functioning elements, at a reasonable cost to manufacture, and by employing only readily available materials.

Therefore, it is an object of this invention to provide an improved composition and method of applying a composition of (a) between about 10 and 15 percent vitamin C, plus or minus 10 percent, by weight to volume, (b) a viscosity agent, and (c) water as the remainder of the composition to healthy surface tissue overlying unhealthy tissue to be treated by radiation therapy for thereby abating dermatitis, mucositis, and esophagitis normally attendant with radiation therapy, the method comprising the steps of identifying the healthy surface tissue in the path of a radiation beam proposed to treat the unhealthy tissue, the identified healthy tissue being pretreated with vitamin C to increase the concentration of ascorbic acid in the identified healthy tissue; applying the composition to the identified healthy tissue; waiting a period of time of about at least one hour prior to radiation therapy so as to allow the vitamin C of the composition to increase the concentration of ascorbic acid in the healthy tissue whereby free radicals from ensuing radiation therapy are scavenged by the increased concentration of ascorbic acid in the healthy tissue; applying therapeutic radiation to the pretreated healthy tissue and the unhealthy tissue in a predetermined target dosage so that unhealthy tissue will be destroyed but so that the increased concentration of ascorbic acid in the healthy tissue will scavenge free radicals from the applied radiation; and scavenging free radicals from the applied radiation by the increased concentration of ascorbic acid in the healthy tissue so that dermatitis, mucositis, and esophagitis normally resulting from radiation therapy are abated.

Another object of the invention is to abate dermatitis, mucositis and esophagitis normally attendant as side effects of radiation therapy.

A further object of this invention is to allow for a predetermined target radiation dosage to be delivered quicker and more reliably than previously possible.

A further object of this invention is to ameliorate inflammation of skin, esophagus and mucosal surfaces.

A further object of this invention is to coat the epidermis, mucosal or esophagal surfaces prior to radiation therapy.

A further object of this invention is modify healthy tissue to greater tissue concentrations of ascorbic acid so that during radiation therapy free radicals from x-rays are quenched or scavenged by ascorbic acid.

A further object of this invention is to protect target tissue with greater resistance to radiation damage.

A further object of this invention is to provide fractionation whereby maximum damage is inflicted on cancerous tissue and minimal damage is inflicted on healthy tissue.

The foregoing has outlined some of the more pertinent objects of this invention. These objects should be construed to be merely illustrative of some of the more prominent features and applications of the present invention. Many other beneficial results can be attained by applying the disclosed invention in a different manner or by modifying the invention within the scope of the disclosure. Accordingly, other objects and a fuller understanding of the invention may be had by referring to the summary of the invention and the detailed description of the preferred embodiment in addition to the scope of the invention defined by the claims taken in conjunction with the accompanying drawings.

SUMMARY OF THE INVENTION

The invention is defined by the appended claims with the specific embodiment shown in the attached drawings. For the purpose of summarizing the invention, the invention may be incorporated into an improved composition for abating dermatitis, mucositis, and esophagitis normally resulting from radiation therapy, comprising, in combination between about 10 and 15 percent vitamin C, plus or minus 10 percent, by weight to volume; a viscosity agent; and water as the remainder of the composition.

The vitamin C may be ascorbic acid and the viscosity agent is propylene glycol constituting between about 15 and 20 percent, plus or minus 10 percent, of the composition, the composition being adapted to be applied topically for abating dermatitis and mucositis. The vitamin C may be a salt of ascorbic acid and the viscosity agent is carboxy methyl cellulose constituting between about 1 and 2 percent, plus or minus 10 percent, of the composition, the composition being adapted to be applied internally for abating esophagitis and mucositis. The ascorbic acid and its salts are essentially interchangeable.

The invention may also be incorporated into a method of applying a composition of (a) between about 10 and 15 percent vitamin C, plus or minus 10 percent, by weight to volume, (b) a viscosity agent, and (c) water as the remainder of the composition to healthy surface tissue overlying unhealthy tissue to be treated by radiation therapy for thereby abating dermatitis, mucositis, and esophagitis normally attendant with radiation therapy, the method comprising the steps of identifying the healthy surface tissue in the path of a radiation beam proposed to treat the unhealthy tissue; applying the composition to the identified healthy tissue; and waiting a period of time of about at least one hour prior to radiation therapy so as to allow the vitamin C of the composition to increase the concentration of ascorbic acid in the healthy tissue whereby free radicals from ensuing radiation therapy are scavenged by the now more abundant ascorbic acid in the healthy tissue thereby abating dermatitis, mucositis, and esophagitis normally attendant with radiation therapy.

The invention may also be incorporated into a method of applying a composition containing vitamin C to healthy surface tissue located in the path of a therapeutic radiation beam, comprising the steps of identifying the healthy surface tissue in the path of a radiation beam proposed to treat unhealthy tissue; applying the composition containing the vitamin C to the identified healthy tissue; and waiting a period of time prior to radiation therapy so as to allow the vitamin C of the composition to increase the concentration of ascorbic acid in the healthy tissue.

The composition comprises, in combination between about 10 and 15 percent vitamin C, plus or minus 10 percent, by weight to volume; a viscosity agent; and water as the remainder of the composition. The vitamin C may be ascorbic acid and the viscosity agent is propylene glycol constituting between about 15 and 20 percent, plus or minus 10 percent, of the composition, the composition being adapted to be applied topically for abating dermatitis and mucositis. The vitamin C may be a salt of ascorbic acid and the viscosity agent is carboxy methyl cellulose constituting between about 1 and 2 percent, plus or minus 10 percent, of the composition, the composition being adapted to be applied internally for abating esophagitis and mucositis. The composition is also applied to the healthy tissue after radiation therapy.

The invention may also be incorporated into a method of treating unhealthy tissue, beneath healthy surface tissue, by radiation therapy, comprising the steps of identifying the healthy surface tissue in the path of a radiation beam proposed to treat the unhealthy tissue, the identified healthy tissue being pretreated with vitamin C to increase the concentration of ascorbic acid in the identified healthy tissue; and applying therapeutic radiation to the pretreated healthy tissue and the unhealthy tissue in a predetermined target dosage so that unhealthy tissue will be destroyed but so that the increased concentration of ascorbic acid in the healthy tissue will scavenge free radicals from the applied radiation for thereby abating dermatitis, mucositis, and esophagitis normally attendant with radiation therapy.

The invention may also be incorporated into a method of treating unhealthy tissue, beneath healthy surface tissue, by radiation therapy, comprising the steps of identifying the healthy surface tissue in the path of a radiation beam to be treated, the identified healthy tissue being pretreated by a composition containing between about 10 and 15 percent vitamin C or a salt thereof, plus or minus 10 percent, by weight to volume, a viscosity agent; and water as the remainder of the composition to increase the concentration of ascorbic acid in the identified healthy tissue; applying therapeutic radiation to the pretreated healthy tissue and the unhealthy tissue in a predetermined target dosage so that unhealthy tissue will be destroyed; and scavenging free radicals from the applied radiation by the increased concentration of ascorbic acid in the healthy tissue so that dermatitis, mucositis, and esophagitis normally resulting from radiation therapy are abated.

The composition comprises in combination between about 10 and 15 percent vitamin C, plus or minus 10 percent, by weight to volume; a viscosity agent; and water as the remainder of the composition. The vitamin C may be ascorbic acid and the viscosity agent is propylene glycol constituting between about 15 and 20 percent, plus or minus 10 percent, of the composition, the composition being adapted to be applied topically for abating dermatitis and mucositis. The vitamin C may be ascorbic acid or a salt thereof and the viscosity agent is carboxy methyl cellulose constituting between about 1 and 2 percent, plus or minus 10 percent, of the composition, the composition being adapted to be applied internally for abating esophagitis and mucositis.

Lastly, the present invention may also be incorporated into an improved method of applying a composition of (a) between about 10 and 15 percent vitamin C or a salt thereof, plus or minus 10 percent, by weight to volume, (b) a viscosity agent, and (c) water as the remainder of the composition to healthy surface tissue overlying unhealthy tissue to be treated by radiation therapy for thereby abating dermatitis, mucositis, and esophagitis normally attendant with radiation therapy, the method comprising the steps of identifying the healthy surface tissue in the path of a radiation beam proposed to treat the unhealthy tissue, the identified healthy tissue being pretreated with vitamin C to increase the concentration of ascorbic acid in the identified healthy tissue; applying the composition to the identified healthy tissue; waiting a period of time of about at least one hour prior to radiation therapy so as to allow the vitamin C of the composition to increase the concentration of ascorbic acid in the healthy tissue whereby free radicals from ensuing radiation therapy are scavenged by the increased concentration of ascorbic acid in the healthy tissue; applying therapeutic radiation to the pretreated healthy tissue and the unhealthy tissue in a predetermined target dosage so that unhealthy tissue will be destroyed but so that the increased concentration of ascorbic acid in the healthy tissue will scavenge free radicals from the applied radiation; and scavenging free radicals from the applied radiation by the increased concentration of ascorbic acid in the healthy tissue so that dermatitis, mucositis, and esophagitis normally resulting from radiation therapy are abated.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the disclosed specific methods and compositions may be readily utilized as a basis for modifying or designing other structures for carrying out the same purposes of the present invention. It should be realized by those skilled in the art that such equivalent methods and compositions do not depart from the spirit and scope of the invention as set forth in the appended claims.

BRIEF DESCRIPTION OF THE DRAWINGS

For a fuller understanding of the nature and objects of the present invention, reference should be had to the following detailed description taken in conjunction with the accompanying drawings in which:

FIG. 1 is a perspective view of radiation therapy to a region in the path of a radiation beam provided with a topical application of the composition in accordance with the principles of the present invention.

FIG. 1a is an enlarged sectional showing of that portion of the patient being treated.

Similar reference characters refer to similar parts throughout the several Figures.

DETAILED DESCRIPTION OF THE INVENTION

Figure 3:
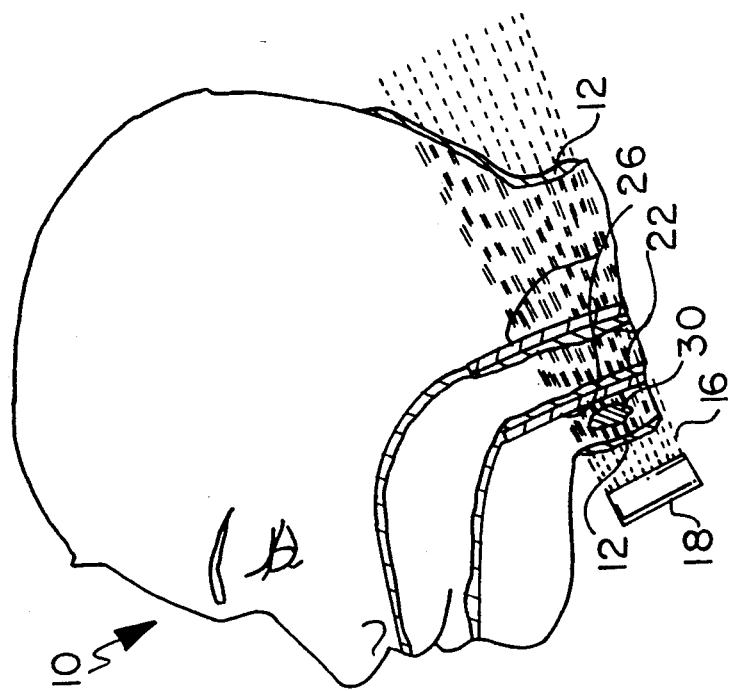
FIG. 3 is a perspective view of the composition of the present invention as applied for an internal application of the composition in the path of a radiation beam during radiation therapy.
Figure 2:
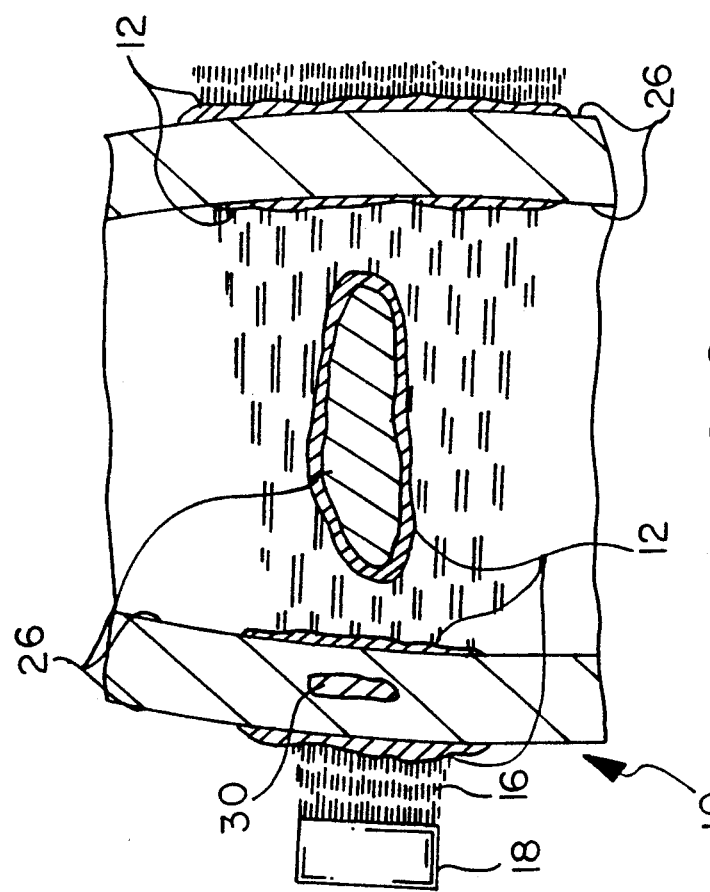
FIG. 2 is a perspective view of the composition of the present invention as applied for oral application in the path of a radiation beam.

Shown in FIGS. 1 through 3 are various views of the primary embodiment of the skin treatment composition constructed in accordance with the principles of the preferred embodiment of the present invention.

From an overview standpoint, the skin treatment composition is adapted for use with a human patient 10 having a condition that necessitates the patient undergoing radiation treatment. Patients undergoing radiation treatment experience dermatitis, mucositis and esophagitis as normal side effects of radiation therapy. However, an application of a composition comprising vitamin C, or ascorbic acid or the salt of ascorbic acid, applied to the skin of the patient prior to radiation therapy substantially prevents the normal expected radiation treatment side effects. See FIGS. 1 through 3.

For the purposes of this patent application, the term Vitamin C is intended to include ascorbic acid as well as its salts. Further, ascorbic acid and its salts are considered essentially equivalent for most applications.

More specifically, the composition 12 comprises between about 10 and 15 percent vitamin C, plus or minus 10 percent, by weight to volume. The vitamin C element is vitamin C, ascorbic acid or the salt of ascorbic acid. Healthy tissue damage resulting from radiation therapy is caused by free radicals. Free electrons are generated by high energy photons or electrons impacting atomic electron shells or are part of a primary electron beam. Subsequent energy transfer is caused by the creation of radicals from the free electrons. The major radical species are superoxide, singlet oxygen, and hydroxide radical. These species are highly reactive. The radicals, therefore, will oxidize nearby structural and enzymatic proteins and lipids. The oxidation results in cell damage and death. The vitamin C molecules act as a scavenger or quencher of the free radicals. The vitamin C molecules are oxidized thereby sparing other potential targets in the immediate vicinity of the vitamin C molecules. The presence of vitamin C thereby prevents oxidative tissue damage. The active part of the vitamin C molecule with respect to oxidation is the -ene diol group. The -ene diol group is oxidized as a result of exposure to the radicals and thereby yields a dehydroascorbic acid. The concentration of vitamin C in the tissue is the limiting factor for preventing oxidative tissue damage.

A typical radiation therapy schedule for Cervical Cancer comprises radiation beam 16 of 4 million electron volts from a linear accelerator 18 for a total dosage of 5040 rads. Each fractional dose is equal to 180 rads applied in 28 fractions. For the treatment of Lung Cancer, a linear accelerator radiation beam of 4 million electron volts for a total dosage between about 6000 rads and 7000 rads is required. Each fractional dose is equal to between about 180 rads and 200 rads applied in between about 30 and 39 fractions. However, Head and Neck Cancers require a linear accelerator radiation beam of 4 million electron volts for delivering a total dosage of radiation equal to 6120 rads. 34 fractions of 180 rads are applied for achieving the 6120 total dosage. Typically, each fraction is an equal dosage of radiation given daily Monday through Friday with no radiation exposure during Saturday or Sunday.

The composition further comprises a viscosity agent. The remainder of the composition is comprised of water. The patient, nurse, radiotherapist or attending physician can apply between about 10 and 15 percent aqueous solution of vitamin C to the skin of the treatment areas to be subjected to radiation. Both the entrance sites and exit sites are treated about one hour prior to the radiation treatments. The patient surprisingly shows no skin inflammation or irritation during the entire course of radiation therapy or thereafter as a result of pretreatment with the composition. The skin treatment composition will not cause irritation nor discomfort as a resultant of using the composition.

To abate dermatitis and mucositis, the composition comprises ascorbic acid to act as the scavenger or quencher of the free radicals. Furthermore, propylene glycol constituting between about 15 and 20 percent, plus or minus 10 percent, of the composition is used as the viscosity agent. For abating dermatitis and mucositis the composition is adapted to be applied topically to surface tissues prior to or after radiation treatment. The composition is applied even if no radiation fraction is received on a given day during radiation treatment. The surfaces tissues comprise mucosal membranes, esophagus and urinary bladder.

To abate esophagitis the composition 22 is applied internally. For abating esophagitis, the composition comprises an ascorbic acid at a lower concentration or preferably a salt of ascorbic acid to avoid discomfort of high acidity. The salt of ascorbic acid acts as the scavenger or quencher of the free radicals. Additionally, carboxy methyl cellulose constituting between about 1 and 2 percent, plus or minus 10 percent, of the composition is used as the viscosity agent to facilitate the internal application of the composition. The composition is drunk daily by a patient during radiation treatment even if no fraction of radiation treatment is received on a given day.

The composition is preferably stored as a two part mixture. Part A comprises the scavenging agent. Part B comprises the viscosity agent and water. Prior to application of the composition Part A and Part B are combined within a single container. The combined composition is discarded one week subsequent to the combination of Parts A and B to ensure the composition contains a scavenging agent level that is maintained at a therapeutic level. Preferably, the vitamin C is a solution sold by Rugby Pharmaceutical with a viscosity agent added thereto.

In the operation and use of the apparatus of the present invention, there is provided a method of treating skin. The above descriptions relate to a skin treatment composition of therapeutic use comprising vitamin C or its salts for the prevention of dermatitis, mucositis and esophagitis as side effects in humans of radiation therapy.

More specifically, the method includes applying a composition by a patient, nurse, radiotherapist or physician to a healthy surface tissue 26 that is in the path of a radiation beam or adjacent an unhealthy tissue 30 to be treated by radiation therapy for thereby abating dermatitis, mucositis and esophagitis normally attendant with radiation therapy. The composition comprises between about 10 and 15 percent vitamin C, plus or minus 10 percent, by weight to volume, a viscosity agent, and water as the remainder of the composition as described above. The method comprises a number of steps in combination. The first step is identifying the healthy surface tissue in the path of a radiation beam being proposed to treat the unhealthy tissue.

FIG. 1 illustrates unhealthy tissue beneath the skin, as for example prostate cancer. FIG. 2 illustrates a cancerous tumor in deep tissue, as for example a parotid gland tumor, showing protection to a patient's tongue, and oral mucosa and external skin. FIG. 3 illustrates treatment of a neck tumor such as laryngeal cancer with protection to external skin and esophageal mucosa.

The next step is applying the composition to the identified healthy tissue. The composition is also applied to adjacent tissue surfaces for mucosal applications. Finally waiting a period of time, normally of about at least one hour, prior to radiation therapy so as to allow the vitamin C of the composition to increase the concentration of ascorbic acid in the healthy tissue. Free radicals from ensuing radiation therapy are then scavenged by the increased concentration of ascorbic acid in the healthy tissue thereby abating dermatitis, mucositis, and esophagitis normally attendant with radiation therapy.

In the operation and use of the present invention, there is provided an alternate method of treating unhealthy tissue, beneath health surface tissue in the beam path of a radiation beam, by radiation therapy. The alternate method comprises a number of steps in combination. The first step is identifying the healthy surface tissue in the path of a radiation beam being proposed to treat the unhealthy tissue. The identified healthy tissue is then pretreated by a composition containing between about 10 and 15 percent vitamin C, plus or minus 10 percent, by weight to volume, a viscosity agent and water as the remainder of the composition to increase the concentration of ascorbic acid in the identified healthy tissue. The next step is applying therapeutic radiation to the pretreated healthy tissue and unhealthy tissue in a predetermined target dosage so that unhealthy tissue will be destroyed. The method includes the further step of scavenging free radicals from the applied radiation by the increased concentration of ascorbic acid in the healthy tissue so that dermatitis, mucositis, and esophagitis normally resulting from radiation therapy are abated.

A chemical reaction giving rise to more free radicals continues for a period of time, at least 30 minutes, subsequent to termination radiation exposure to the treated skin. The chemical reaction within the exposed tissues causes dermatitis, mucositis, and esophagitis to develop in the treated tissues even though the tissues are no longer exposed to radiation. Therefore, the composition is reapplied to the tissues subsequent to exposure to radiation for preventing dermatitis, mucositis, and esophagitis as post radiation exposure side effects.

The present disclosure includes that contained in the appended claims as well as that of the foregoing description. Although this invention has been described in its preferred forms with a certain degree of particularity, it is understood that the present disclosure of the preferred form has been made only by way of example and numerous changes in the details of construction and combination and arrangement of parts may be resorted to without departing from the spirit and scope of the invention.

Now that the invention has been described, what is claimed is:

1. A method of applying a composition containing vitamin C to healthy surface tissue located in the path of a therapeutic radiation beam, wherein the undesired side effects of radiation therapy are abated, the method comprising the steps of:

identifying the healthy surface tissue in the path of a radiation beam proposed to treat unhealthy tissue;
   applying the composition containing the vitamin C to the identified healthy tissue;
   waiting a period of time sufficient to allow the vitamin C of the composition to increase the concentration of ascorbic acid in the healthy tissue;
   again applying the composition containing the vitamin C to the identified healthy tissue;
   again waiting a period of time sufficient to allow the vitamin C of the composition to further increase the concentration of ascorbic acid in the healthy tissue; and
   exposing the unhealthy tissue and healthy tissue to radiation therapy subsequent to at least one of the waiting steps.

2. The method as set forth in claim 1 wherein the composition comprises, in combination:

between about 10 and 15 percent vitamin C within the limits of solubility;
   a viscosity agent; and
   water as the remainder of the composition.

3. The method as set forth in claim 2 wherein the vitamin C is ascorbic acid and the viscosity agent is propylene glycol constituting between about 15 and 20 percent of the composition, the composition being adapted to be applied topically for abating dermatitis and mucositis.

4. The method as set forth in claim 2 wherein the vitamin C is a salt of ascorbic acid and the viscosity agent is carboxy methyl cellulose constituting between about 1 and 2 percent of the composition, the composition being adapted to be applied internally for abating esophagitis.

5. The method as set forth in claim 1 wherein the composition is applied to the healthy tissue after radiation therapy.

6. A method of treating unhealthy tissue, adjacent to healthy surface tissue, by radiation therapy, comprising the steps of:

identifying the healthy surface tissue in the path of a radiation beam proposed to treat the unhealthy tissue, the identified healthy tissue being pretreated by applying a composition containing vitamin C to increase the concentration of ascorbic acid in the identified healthy tissue; and
   applying therapeutic radiation to the pretreated healthy tissue and the unhealthy tissue in a predetermined target dosage so that the unhealthy tissue will be destroyed but so that dermatitis, mucositis, and esophagitis normally attendant with radiation therapy will be abated.

7. A method of delivering radiation therapy, comprising the steps of:

identifying the healthy surface tissue in the path of a radiation beam to be treated, the identified healthy tissue being pretreated by applying a composition containing vitamin C, a viscosity agent, and water as the remainder of the composition to increase the concentration of ascorbic acid in the identified healthy tissue;
   again applying the composition containing the vitamin C to the identified healthy tissue; and
   applying therapeutic radiation to the pretreated healthy tissue and the unhealthy tissue in a predetermined target dosage so that the unhealthy tissue will be destroyed; and scavenging free radicals from the applied radiation by the increased concentration of ascorbic acid in the healthy tissue so that dermatitis, mucositis, and esophagitis normally resulting from radiation therapy are abated.

8. The method as set forth in claim 7 wherein the composition comprises, in combination:

between about 10 and 15 percent vitamin C by weight to volume;

a viscosity agent; and water as the remainder of the composition.

9. The method as set forth in claim 8 wherein the vitamin C is ascorbic acid and the viscosity agent is propylene glycol constituting between about 15 and 20 percent of the composition, the composition being adapted to be applied topically for abating dermatitis and mucositis.

10. The method as set forth in claim 8 wherein the vitamin C is a salt ascorbic acid and the viscosity agent is carboxy methyl cellulose constituting between about 1 and 2 percent of the composition, the composition being adapted to be applied internally for abating esophagitis.

11. A method of applying a composition of (a) between about 10 and 15 percent vitamin C by weight to volume, (b) a viscosity agent, and (c) water as the remainder of the composition to healthy surface tissue overlying unhealthy tissue to be treated by radiation therapy for thereby abating dermatitis, mucositis, and esophagitis normally attendant with radiation therapy, the method comprising the steps of:

identifying the healthy surface tissue in the path of a radiation beam proposed to treat the unhealthy tissue, the identified healthy tissue being pretreated with vitamin C to increase the concentration of ascorbic acid in the identified healthy tissue;

applying the composition to the identified healthy tissue;

waiting a period of time of about at least one hour prior to radiation therapy so as to allow the vitamin C of the composition to increase the concentration of ascorbic acid in the healthy tissue whereby free radicals from ensuing radiation therapy are scavenged by the increased concentration of ascorbic acid in the healthy tissue;

applying therapeutic radiation to the pretreated healthy tissue and the unhealthy tissue in a predetermined target dosage so that the unhealthy tissue will be destroyed but so that the increased concentration of ascorbic acid in the healthy tissue will scavenge free radicals from the applied radiation; and scavenging free radicals from the applied radiation by the increased concentration of ascorbic acid in the healthy tissue so that dermatitis, mucositis, and esophagitis normally resulting from radiation therapy are abated.

* * * * *